United States Patent [19]
Sattler et al.

[11] Patent Number: 5,561,166
[45] Date of Patent: Oct. 1, 1996

[54] UREA/LACTATE TOPICAL COMPOSITIONS FOR DRY SKIN

[75] Inventors: Henning Sattler, Hamburg; Horst Wenck, Norderstedt, both of Germany; Sven Thormählen, Greenwich, Conn.; Karlheinz Schrader, Holzminden, Germany

[73] Assignee: Beiersdorf, Inc., Norwalk, Conn.

[21] Appl. No.: 100,094

[22] Filed: Jul. 28, 1993

[51] Int. Cl.$^6$ ............................ A61K 47/12; A61K 31/17
[52] U.S. Cl. ........................ 514/784; 514/588; 514/844; 514/847
[58] Field of Search ................................ 514/847, 784, 514/588

[56] References Cited

U.S. PATENT DOCUMENTS

| | | | |
|---|---|---|---|
| 4,105,782 | 8/1978 | Yu et al. | 424/283 |
| 4,246,261 | 1/1981 | Van Scott et al. | 424/240 |
| 4,703,041 | 10/1987 | Weber et al. | 514/847 |
| 5,091,171 | 2/1992 | Yu et al. | |
| 5,162,378 | 11/1992 | Guthauser . | |
| 5,215,759 | 6/1993 | Mausner | 514/847 |
| 5,216,033 | 6/1993 | Pereira et al. | 514/847 |

OTHER PUBLICATIONS

Ashton, H., et al., Br. J. Dermatol. 84: 194–196 (1971).
Blair, C., Br. J. Dermatol. 94: 145–153 (1976).
Harry et al, The Principle and Pratice of Modern Cosmetics, 1963, vol. 2, Cosmetic Materials, pp. 248, 249 & 520–523.
Blichmann, C. W. and Serup, J., Acta Derm. Venereol. (Stockh.) 68: 284–290 (1988).
Cecil's Textbook of Medicine, 17th ed., W. B. Saunders Co., Philadelphia, 1985, pp. 2240–2241.
Leveque, J. L., J. Soc. Cosmet. Chem. 82: 171–177 (1987).
Martindale Pharmacopeia, 29th edition, citing Report No. 179 of the General Practitioner Research Group, Practitioner 210: 294 (1973).
Physicians' Desk Reference, 45th ed., 1991, p. 2198.
Rogers, R. S., et al., J. Am. Acad. Dermatol. 21: 714–1989 (1991).
Swanbeck, G., Acta Derm. Venereol. 48: 123–127 (1968).
Tronnier, H., Ärztl. Kosmetologie 10: 291–308 (1980) * Untranslated version in German.
Van Scott, E. J., and Yu, R. J., Cutis, 43: 222–228 (1989).

*Primary Examiner*—Shelley A. Dodson
*Attorney, Agent, or Firm*—St. Onge Steward Johnston & Reens

[57] ABSTRACT

Methods and compositions for the treatment of dry skin involve the topical application to affected sites of a composition comprising from about 1% to about 12% by weight of urea and from about 1% to about 10% by weight of and alkali or an earth metal salt of lactic acid such as sodium, potassium or calcium lactate or a mixture of these salts in water-in-oil emulsions. In lotion embodiments, the emulsion typically contains from about 1% to about 10% by weight, more narrowly from about 2% to about 5% by weight, lactate and from about 1% to about 10% by weight, more narrowly from about 2% to about 5% by weight, urea. In cream embodiments, the emulsion typically contains from about 1% to about 5% by weight, more narrowly from about 2% to about 4% by weight, lactate, and from about 3% to about 15% by weight, more narrowly from about 5% to about 10% by weight, urea. Application of the compositions of the invention to the skin controls transepidermal water loss and minimizes disturbance of the epidermal barrier layer.

22 Claims, 12 Drawing Sheets

UREA/LACTATE TOPICAL COMPOSITIONS FOR DRY SKIN

TECHNICAL FIELD

This invention relates to the treatment of dry skin using a composition containing urea and lactate.

BACKGROUND OF THE INVENTION

Dry skin or xerosis is a common condition that frequently requires therapeutic intervention. Xerosis is characterized by aggregated desquamating corneocytes with the appearance of fine white scales; clinically, it is often accompanied by decreased mechanical flexibility of the stratum corneum, fine fissures, inflammation, and sensations of itching and burning. The condition is believed to stem from impaired water-binding capability in the stratum corneum. It is aggravated by exposure to low temperatures and low indoor humidity in winter months commonly found in northern climates. Furthermore, other adverse environmental conditions such as exposure to detergents and solvents, subclinical dyskeratotic disorders and age support the clinical manifestation of xerosis.

Numerous humidifying topical preparations containing emollients and humectants have been used over the years for the treatment of dry skin, as well as for more acute dermatological disorders including ichthyosis, psoriasis, actinic damage, eczema, and the like which exhibit dry skin symptoms. Many such preparations primarily affect the skin's outer layer, the stratum corneum, and act as a partial replacement for the damaged stratum corneum.

In addition to traditional topical treatment with emollients, preparations with physiologically active ingredients have been suggested for the treatment of dry skin. High concentrations of urea (10% or higher), for example, have been suggested for the therapy of ichthyosis and other hyperkeratotic conditions (Swanbeck, G., *Acta Derm. Venereol.* 48:123–127 (1968)); urea appeared to exhibit both a water-binding function and a keratolytic activity, though a double blind study was not carried out (ibid.). In a brief review, Ashton, et al., suggested that higher urea concentrations, i.e., 40% to 48%, were beneficial in a double blind study, and that the dermatological importance of urea may also stem from its generally accepted property of unfolding proteins, thus solubilizing and/or denaturing them (Ashton, H., et al., *Br. J. Dermatol.* 84:194–196 (1971)).

Van Scott and Yu suggested that alpha-hydroxy and alpha keto acids in concentrations up to 12% be used for the treatment of dry skin, ichthyosis, follicular hyperkeratosis and other conditions (Van Scott, E. J., and Yu, R. J., *Cutis,* 43:222–228 (1989)). Lactic acid and glycolic acid were especially preferred for dry skin and analogous conditions (ibid., page 222). However, compositions containing these acids exhibit a very acidic milieu at pH values smaller than 2. Repeated topical application of compositions with such low pH values irritates the skin. It is therefore necessary to use these alpha-hydroxy acids in neutralized or at least partially neutralized forms. Topical application of the sodium salts of lactic and glycolic acid were found by the same investigators to be ineffective. They subsequently suggested that lactic and glycolic acid be used with amphoteric compounds such as amino acids or peptides and/or that polymeric forms of the alpha-hydroxy acids be employed (U.S. Pat. No. 5,091,171 to Yu and Van Scott). Compositions of this type that contain ammonium lactate have been shown to be efficacious in the treatment of dry skin (Rogers, R. S., et al., *J. Am. Acad. Dermatol.* 21:714–1989 (1991)). A currently marketed product under this invention is LacHydrin® (Westwood-Squibb Pharmaceuticals). It contains 14.0% ammonium lactate (equivalent to 12% lactic acid). It must be dispensed in the United States as a prescription drug.

Blair reported some findings about the action of a Calmurid™ ointment containing lactic acid, betaine, and 10% urea in the treatment of ichthyosis (Blair, C., *Br. J. Dermatol.* 94:145–153 (1976)). However, both the ointment base alone and the ointment with the active ingredients were effective in reducing the thickness of the skin scales (ibid., on page 150), and apparently only 11 patients participated in the study. In a double-blind trial involving 55 patients, Calmurid™ cream was no more effective than aqueous cream in the treatment of hyperkeratosis (*Martindale Pharmacopeia,* 29th edition, citing Report No. 179 of the General Practitioner Research Group, *Practitioner* 210:294 (1973)).

Urea has been suggested as an ingredient of other topical preparations having other active ingredients including cetyl dimethicone copolyol and silicone (U.S. Pat. No. 5,162,378 to Guthauser) and hydrocortisones (e.g., Carmol™, *Physicians' Desk Reference,* 45th ed., 1991, page 2198). Unless special emulsifiers or ingredients are employed with silicones, however, it is difficult to use them because of the instability of emulsions containing them. Use of topical steroid compositions have been reported to be associated with adverse effects after longterm usage, including epidermal and dermal atrophy, decreased collagen synthesis and the hazard of systemic absorption (*Cecil's Textbook of Medicine,* 17th ed., W. B. Saunders Co., Philadelphia, 1985, pages 2240–2241).

SUMMARY OF THE INVENTION

It is an object of the invention to provide a new cosmetically acceptable topical composition for the treatment of dry skin and related dermatological disorders.

It is a more specific object of the invention to provide a topical composition that is efficacious for the treatment or prevention of dry skin, exhibits a good level of skin compatibility, and acts primarily on the stratum corneum.

These and other objects are accomplished by the present invention, which provides compositions for the treatment and prevention of dry skin. In the practice of this invention, compositions containing an alkali or earth metal salt of lactic acid and urea are applied to affected skin sites. Against the previous teaching by Van Scott and Yu, according to which application of alkali and earth salts of lactic acids containing compositions is described to be physiologically inactive, these salts were found to be highly effective when combined with urea. Preferred compositions are water-in-oil emulsions containing from about 1% to about 12% by weight urea and from about 1% to about 10% by weight of sodium, potassium or calcium lactate or mixtures of these salts. In lotion embodiments, the emulsion typically contains from about 1% to about 10%, more narrowly from about 2% to about 5% by weight, urea. One particularly preferred embodiment contains about 5% sodium lactate and about 5% urea. In cream embodiments, the emulsion typically contains from about 1% to about 5% by weight, more narrowly from about 2% to 4% by weight, lactate, and from about 3% to 15% by weight, more narrowly from about 5% to 10% by weight, urea. One particularly preferred embodiment contains about 2.5% lactate and about 10% urea.

DETAILED DESCRIPTION OF THE INVENTION

Figure 1:
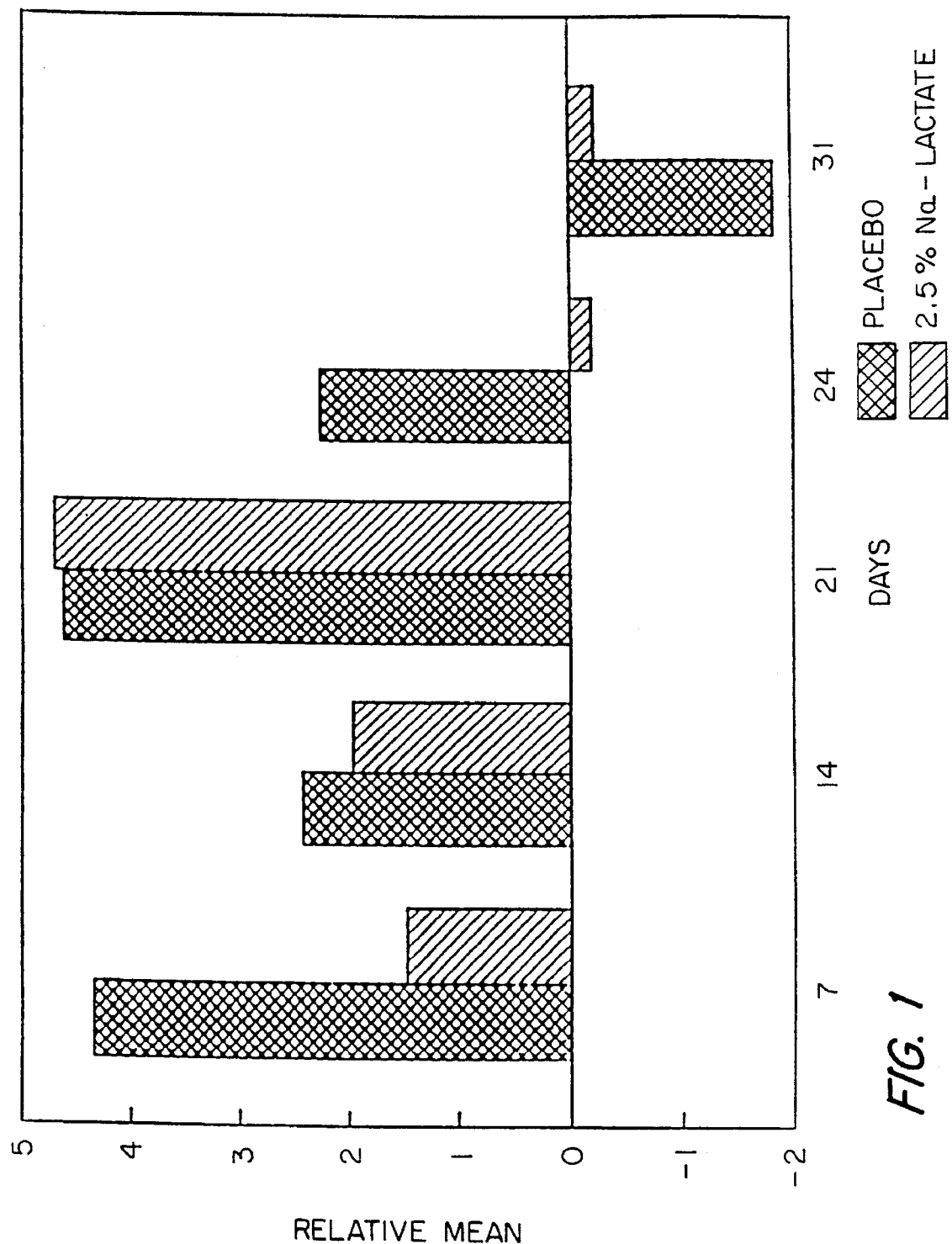
FIG. 1 gives relative mean moisture content values relative to the baseline in a randomized double-blinded clinical test in which a 2.5% sodium lactate containing water-in-oil emulsion (hatched bars) is compared to the vehicle base without the sodium lactate (cross-hatched bars). Test materials were applied to severely dry skin in 20 subjects twice daily for 21 consecutive days, and evaluations continued for 10 days after discontinuing treatment.

This invention is based upon the finding that dry skin can be efficaciously treated or prevented by applying a topical composition containing urea and sodium lactate in water-in-oil emulsions formulated so that, on application to affected skin areas, the clinical signs of dry skin are significantly reduced, flakiness of the skin is significantly reduced and the disturbance of the epidermal barrier is minimized as demonstrated by measurements of transepidermal water loss. The finding that sodium lactate in combination with urea is comparable or superior to ammonium lactate controls was unexpected in view of earlier teachings disclosing sodium lactate as physiologically inactive.

The compositions of this invention comprise from about 1% to about 12% by weight urea and from about 1% to about 10% by weight of an alkali or earth metal salt of lactic acid in a cosmetically acceptable water-in-oil emulsion. A water-in-oil emulsion contains an aqueous phase evenly dispersed in a continuous outer oil phase. "Cosmetically acceptable" means suitable for use as a cosmetic, i.e., suitable to be directly applied to the skin for the treatment or prevention of dry skin without the need for a prescription, or special instructions prior to use.

By the term "urea" is meant urea, sometimes called carbamide, and urea derivatives such as alkyl carbamides, particularly those bearing only one or two methyl or ethyl groups, and mixtures thereof. Urea is preferred. As defined and denoted herein, weight percentages of urea, urea derivatives and mixtures thereof are expressed as weight percent urea. Use of embodiments where urea derivatives or mixtures are employed will require appropriate adjustment in levels.

An alkali or earth metal salt of lactic acid such as sodium, potassium or calcium or a mixture of these is employed with urea. Sodium lactate is especially preferred in some embodiments. As defined and denoted herein, all weight percentages of alkali or earth salts of lactic acid are defined as weight percent sodium lactate. Use of embodiments employing other alkali or earth metal salts or salt mixtures will require appropriate adjustment in levels.

The urea and the lactate are formulated in cosmetically acceptable water-in-oil emulsions of the invention in admixture with dermatologically acceptable carriers or vehicles such as lotions and creams that facilitate topical application and, in some cases, provide additional therapeutic benefits as might be brought about, e.g., by moisturizing of the affected skin areas. Typical cream formulations contain from about 1% to about 5% by weight lactate and from about 3% to about 15% by weight urea. Some embodiments contain about 2% to about 4% by weight lactate and from about 5% to about 10% urea. One particularly preferred composition contains about 2.5% by weight sodium lactate and about 10.0% by weight urea.

Typical lotion formulas contain from about 1% to about 10% by weight lactate and from about 1% to about 10% by weight urea. Some embodiments contain from about 2% to about 5% by weight lactate and from about 2% to about 5% by weight urea. One particularly preferred composition contains about 5.0% by weight sodium lactate and about 5.0% by weight urea.

Suitable carriers for lactate and urea include water, fatty alcohols, oils and the like, chosen for their ability to dissolve or disperse the ingredients of this inventions at the concentrations set out above. While the carrier for the lactate and urea can consist of a relatively simple solvent or dispersant such as water or oils, it is generally preferred that the carrier comprise a composition more conducive to topical application, and particularly one which can be layered on the skin to which it is applied so as to localize the application and provide some resistance to washing off by immersion in water or by perspiration. Many such compositions are known in the art, and typically contain water and/or fatty alcohols and emollients such as hydrocarbon oils and waxes, silicon oils, vegetable, animal or marine fats or oils, glyceride derivatives, fatty acids, esters or ethers, lecithin, lanolin and its derivatives, polyhydric alcohols such as glycerol, sterols, and generally also emulsifiers (nonionic, cationic or anionic). These same general ingredients can be formulated into creams or lotions by utilization of different proportions of the ingredients and/or by inclusion of thickening agents such as gums or other forms of hydrophilic colloids. Such compositions are referred to herein as "dermatologically acceptable" carriers.

When applied to affected skin areas for the treatment or prevention of dry skin, the composition of the invention exhibit a number of advantages. The release and diffusion kinetics of the water-in-oil emulsion are different from oil-in-water emulsions, providing a superior biocompatibility and a reduced rate of irritation. After application, the compositions of the invention exhibit an occlusive effect, which controls transepidermal water loss of the skin while minimizing disturbance of the epidermal barrier. In the stratum corneum, the compositions of the invention efficaciously hydrate and lubricate. Thus, application of compositions of the invention to dry skin results in very rapid alleviation of symptoms.

Even though the compositions of the invention are water-in-oil emulsions, they are surprisingly non-greasy after application to the skin, yet they exhibit a pleasant, lubricating effect on the skin. When applied to very dry skin, the compositions do not burn or sting. In comparison tests set out in the next section, the composition where superior in this regard to other commercially available compositions containing only ammonium lactate. With adverse effects diminished, using the composition and method of the invention enhances patient compliance in the treatment of dermatologic disorders exhibiting dry skin symptoms.

The following examples are presented to further illustrate and explain the present invention and should not be taken as limiting in any regard. Unless otherwise indicated, all parts and percentages are by weight, and are based on the weight at the particular stage of the processing being described.

EXAMPLE 1

This Example reports a study comparing and contrasting a dry skin treatment using a urea/lactate composition of this invention with two placebo controls. The composition of this invention contained 2.5% by weight sodium lactate (herein denoted NaLac) and 10.0% by weight urea in a water-in-oil emulsion. The first placebo control comprised the same vehicle base without sodium lactate and urea. The second placebo control comprised the same vehicle base without urea but with 2.5% sodium lactate.

The study was conducted in Hamburg, Germany for a 34-day period from September through October 1991. Twenty female panelists with senile xerotic skin, average age was 59 years, were enrolled in the study, all of whom completed it. Test areas were the lower legs. Products were applied twice daily for 21 days. Evaluations were made on days 0, 7, 14, 21, 24 and 31. Skin moisture content was measured using a corneometer (Tronnier, H., *Arztl. Kosmetologie* 10:291–308 (1980)). The data were calculated as relative to the baseline.

The two placebo controls were compared to each other. The results, summarized in columns 1 and 2 of Table 1 below are plotted in FIG. 1. Moisture levels improve as a result of treatment with placebo controls during the treatment phase; addition of sodium lactate to the vehicle base is not advantageous. Improvement is not sustained during the regression period.

TABLE 1

A Comparison of a Placebo With a Composition of the Invention

| Day | Column 1 Moisture Placebo | Column 2 Moisture 2.5% NaLac | Column 3 Moisture 2.5% NaLac 10.0% Urea | Column 4 Flakiness Placebo | Column 5 Flakiness 2.5% NaLac 10.0% Urea |
|---|---|---|---|---|---|
| 7  | 4.34  | 1.48  | 10.52 | −5.37  | −34.46 |
| 14 | 2.43  | 1.96  | 11.12 | −7.66  | −18.28 |
| 21 | 4.62  | 4.7   | 8.54  | −15.35 | −51.96 |
| 24 | 2.26  | −0.19 | 6.57  | 14.25  | −8.87  |
| 31 | −1.84 | −0.23 | 2.96  | 3.18   | −0.30  |

Figure 2:
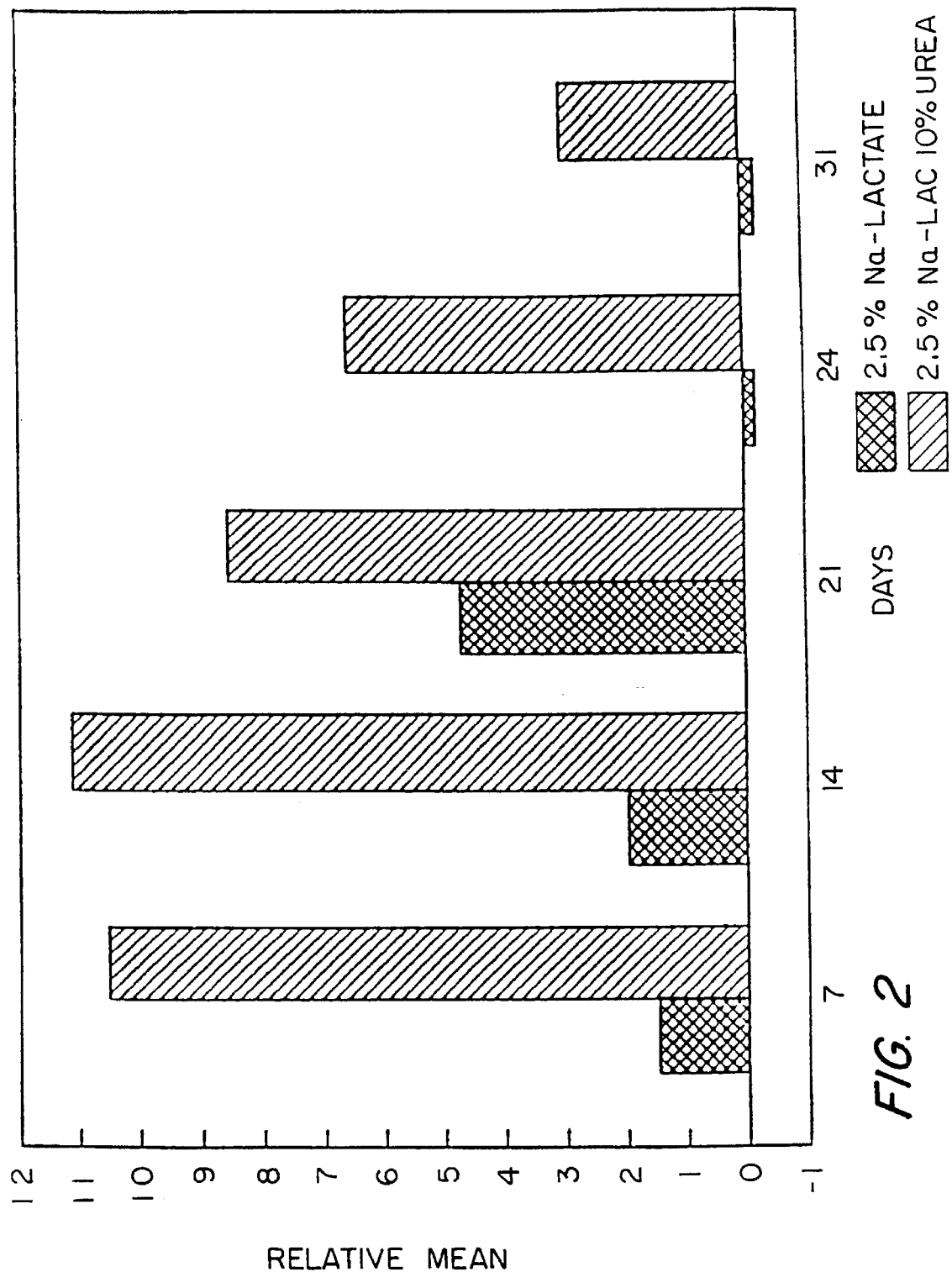
FIG. 2 compares the same 2.5% sodium lactate containing emulsion as above (FIG. 1) with a 2.5% sodium lactate 10% urea containing water-in-oil emulsion of this invention on severely dry skin treated as described in the legend of FIG. 1 above. The data were calculated as mean differences from the baseline.

The sodium lactate placebo was compared to the product of this invention, containing 2.5% by weight sodium lactate and 10.0% by weight urea. The results, summarized in columns 1 and 3 of Table 1 are plotted in FIG. 2. Relative to the control, the composition of this invention exhibits a significant superiority in moisturization capability. This effect is sustained during the regression period.

Figure 3:
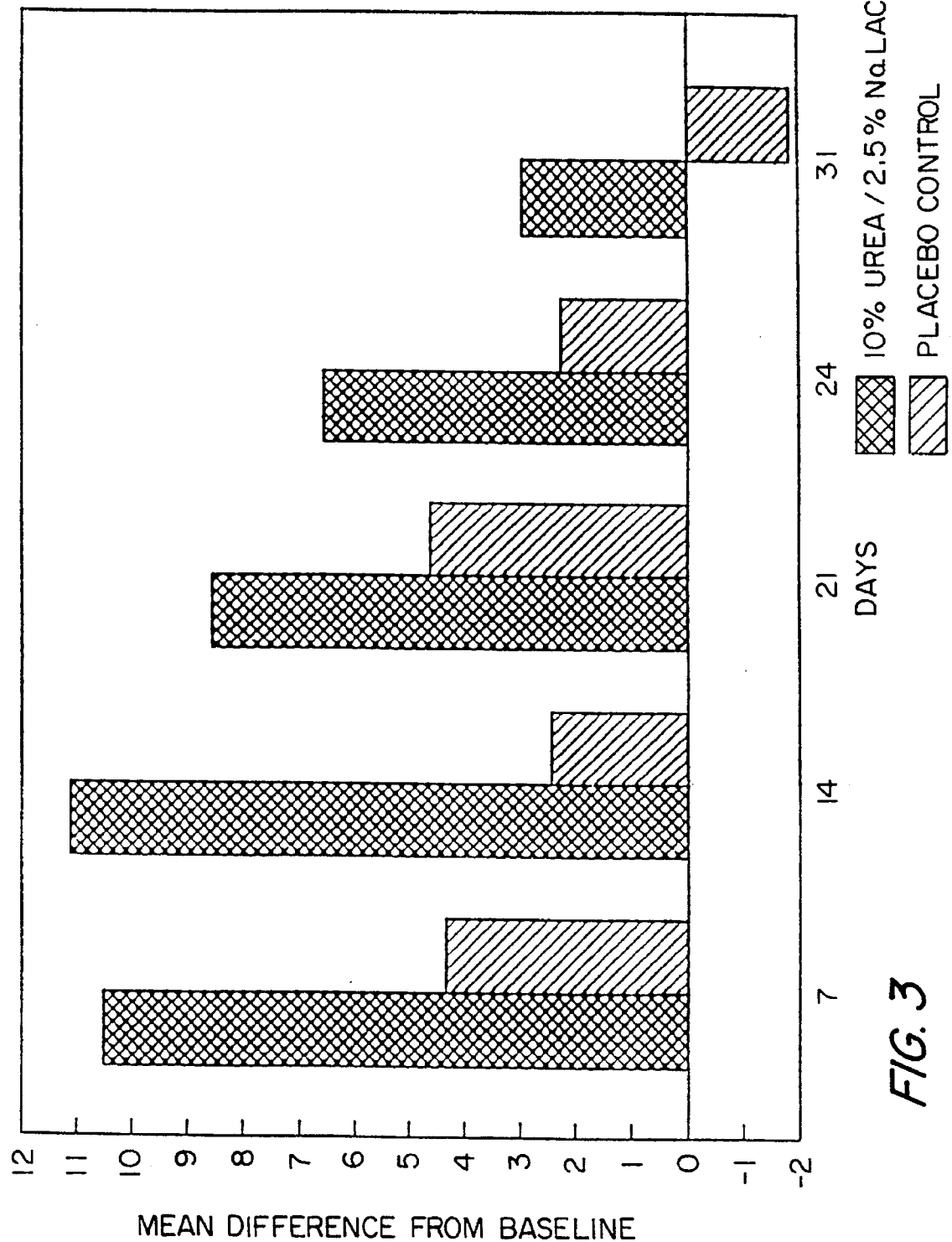
FIG. 3 compares the same 2.5% sodium lactate 10% urea-containing emulsion as described in the legend of FIG. 2 above with the vehicle base without lactate on severely dry skin treated as described in the legend of FIG. 1 above.

The vehicle base alone was compared to the composition of this invention, summarized in columns 2 and 3 of Table 1 and are plotted in FIG. 3. Relative to the control, the composition of this invention exhibits a significant superiority in moisturization capability. This effect is sustained during the regression period.

Parallel to the improvement of dry skin as determined by skin moisture content measurement, skin flakiness was assessed by analysis of D-Squame™ disks (CuDerm Corporation, Dallas, Tex.) using the method of Leveque, J. L.,

*J. Soc. Cosmet. Chem.* 82:171–177 (1987). Skin flakes and scales adhere to transparent tape disks, which are applied in a pressure-controlled fashion. Image analysis of the disks allows quantification of the skin's flakiness.

Figure 4:
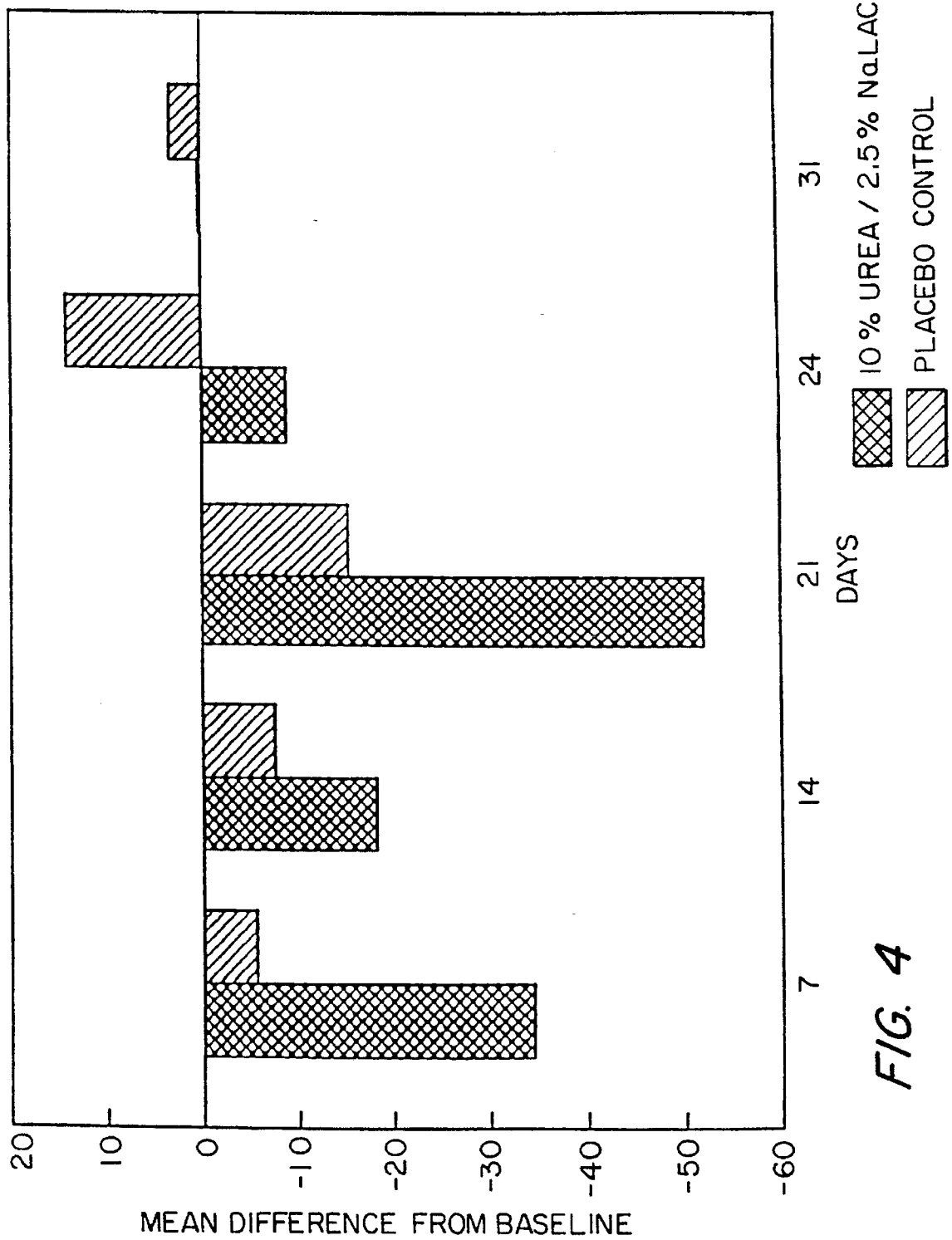
FIG. 4 compares flakiness measured using D'Squame™ disks on the severely dry skin as described in the legend of FIG. 1 above. The 2.5% sodium lactate 10% urea-containing emulsion of this invention as described above is compared to the vehicle cream base without any lactate or urea as described above. The data were calculated as mean differences from the baseline.

The composition of this invention, containing 2.5% by weight sodium lactate and 10.0% by weight urea, was compared to a placebo control comprised of the identical vehicle base but without sodium lactate and urea. The results are summarized in columns 4 and 5 of Table 1 and plotted in FIG. 4.

Flakiness is significantly more reduced in the composition of this invention, compared to the placebo control. The effect is sustained somewhat during the regression period.

The results presented here demonstrate the efficaciousness of the composition of this invention in the treatment of severely dry skin. In combination with urea, sodium lactate is physiologically active in topical application to affected skin areas.

EXAMPLE 2

This study compared and contrasted a dry skin treatment using a urea/lactate composition of this invention with a commercially available dry skin product control containing ammonium lactate. The composition of this invention contained 5% by weight urea and 5% by weight sodium lactate in a water-in-oil emulsion. The control contained 6.2% by weight ammonium lactate (hereinafter abbreviated ammon lactate) in an oil-in-water emulsion.

The study was conducted in Winnipeg, Manitoba for a 35-day period from February through April 1992, during which the average temperature was −3° C. and the average relative humidity was 77.5%. Thirty-one female panelists were enrolled in the study, of whom 27 completed it. The study area was the lower leg. Both legs of each subject initially had a score of grade 3, graded according to the following scale:

0=smooth, no evidence of dryness

1=slightly dry skin

2=moderately dry skin, flaking, peeling

3=severely dry skin, flaking, peeling.

Figure 5:
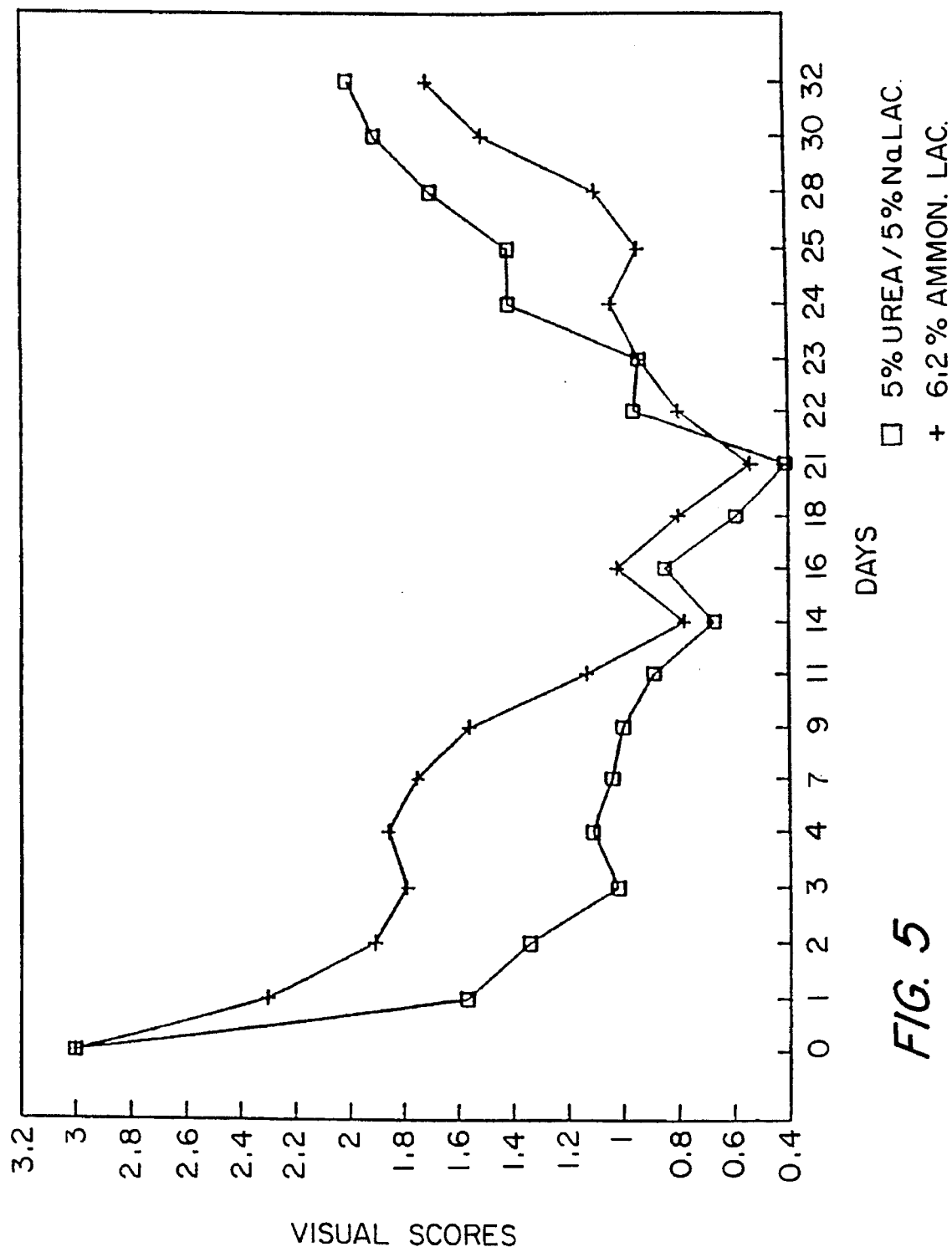
FIG. 5 gives mean visual dry skin scores in a randomized, double-blinded clinical test comparing a 5% sodium lactate 5% urea containing water-in-oil emulsion of this invention with a commercial product containing 6.2% ammonium lactate in an oil-in-water emulsion. Test materials were applied to severely dry skin in 27 subjects twice daily for 21 consecutive days, and evaluations continued for 14 days after discontinuing treatment. On the "Visual Scores" axis, 3.0 denotes severely dry, fissured skin and 0.0 denotes perfectly healthy, moist skin.

Products were applied twice daily, the test material to one leg and the control to the other. The assignments were made in a randomized fashion, the study was double-blinded in design. Products were applied for 21 consecutive days, followed by a 14-day regression period. Evaluations were made on days 0, 1"4, 7, 9, 11, 14, 16, 18, 21–25, 28, 30, 32 and 35. Visual evaluations found the urea/sodium lactate-containing preparation of this invention to be a significantly better moisturizer than the control during the treatment phase. The rapid onset of amelioration of dry skin during the first nine days was pronounced. Flaking and peeling of the skin disappeared in most subjects over the first week, while the control still showed flaking and peeling. FIG. 5 shows the mean visual dry skin scores for both preparations. Actual test data are given in columns 1 and 2 of Table 2 below. Immediately after termination of treatment on day 21, the control product appeared to exhibit better moisture retention, but the effect diminished after the first week of regression.

TABLE 2

A Comparison of an Ammonium Lactate Composition With a Composition of the Invention

| Day | Column 1 Visual Dry Skin Scores 5.0% NaLac | Column 2 Visual Dry Skin Scores 2.5% NaLac 10.0% Urea | Column 3 TEWL 5.0% NaLac 5.0% Urea | Column 4 TEWL 6.2% Ammon Lactate | Column 5 D'Squames 5.0% NaLac 5.0% Urea | Column 6 D'Squames 6.2% Ammon Lactate |
|---|---|---|---|---|---|---|
| 0 | 3.00 | 3.00 | | | | |
| 1 | 1.57 | 2.30 | | | | |
| 2 | 1.34 | 1.91 | | | | |
| 3 | 1.02 | 1.79 | | | | |
| 4 | 1.11 | 1.86 | | | | |
| 7 | 1.04 | 1.75 | −3.48 | −2.28 | −15.64 | −0.24 |
| 9 | 1.00 | 1.56 | | | | |
| 11 | 0.89 | 1.13 | | | | |
| 14 | 0.67 | 0.78 | −4.18 | −3.18 | −9.98 | −7.57 |
| 16 | 0.85 | 1.02 | | | | |
| 18 | 0.59 | 0.80 | | | | |
| 21 | 0.41 | 0.54 | −1.89 | −0.33 | −23.44 | −16.89 |
| 22 | 0.96 | 0.80 | | | | |
| 23 | 1.31 | 0.94 | | | | |
| 24 | 1.41 | 1.04 | | | | |
| 25 | 1.41 | 0.94 | | | | |
| 28 | 1.69 | 0.94 | −1.94 | −0.68 | −2.49 | −3.43 |
| 30 | 1.90 | 1.09 | | | | |
| 32 | 2.00 | 1.70 | | | | |
| 35 | 1.98 | 1.91 | 0.48 | 1.73 | 3.53 | 12.64 |

In addition to visual evaluation, trans-epidermal water loss (TEWL) was recorded with a ServoMed Evaporimeter™ (Stockholm, Sweden) as described by Blichmann, C. W., and Serup, J., *Acta Derm. Venereol.* (Stockh.) 68: 284–290 (1988).

Figure 6:
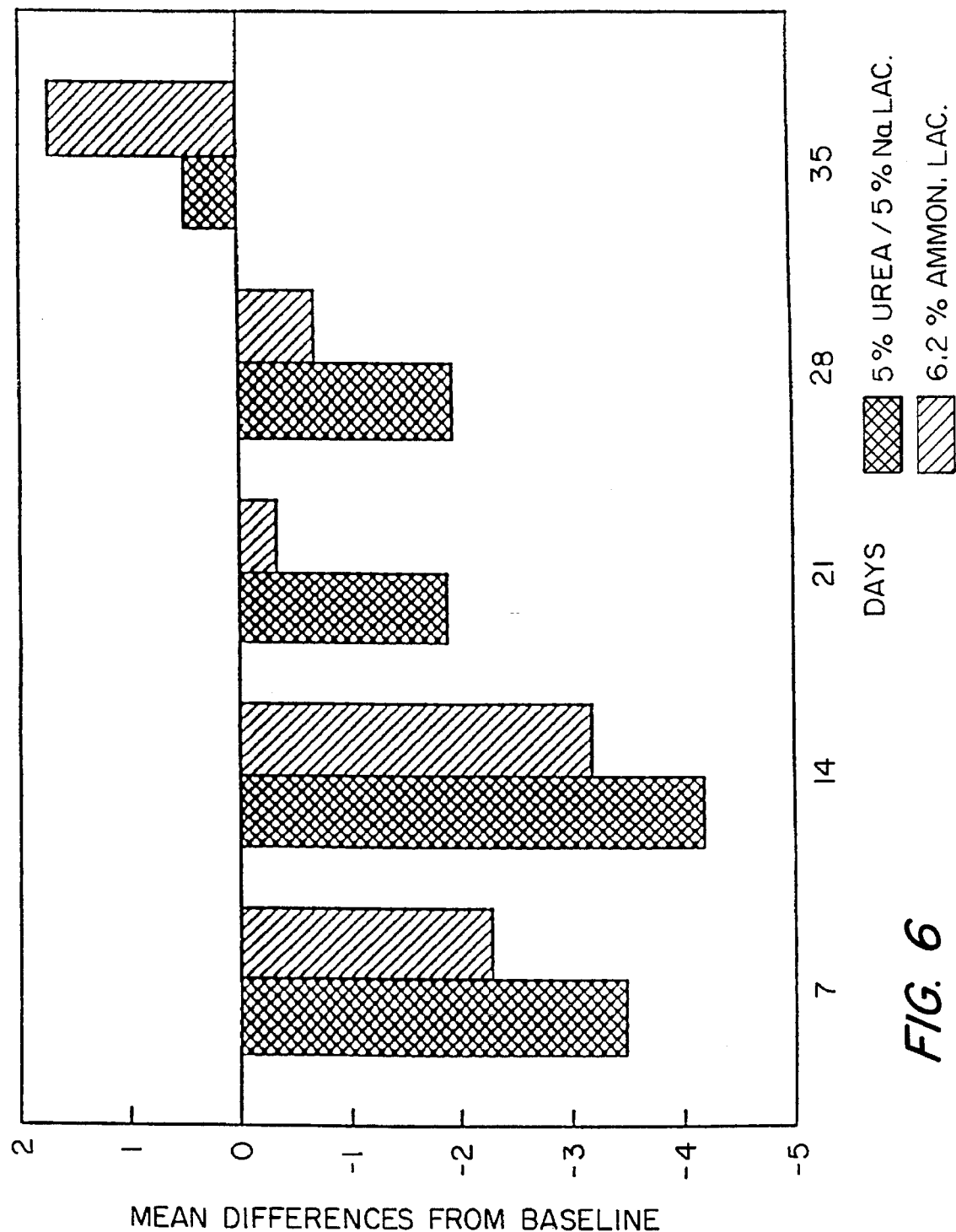
FIG. 6 compares trans-epidermal water loss measured on the severely dry skin treated as described in the legend of FIG. 5 above. The data were calculated as mean differences from the baseline. The cross-hatched bars depict data for treatment using the composition of this inventions, and the hatched bars depict data for the ammonium lactate control.

TEWL evaluations were made on days 0, 7, 14, 21, 28 and 35. As set out in FIG. 6, which shows mean differences calculated as post-treatment minus baseline, the TEWL data indicated significant overall differences between the samples. Data are given in columns 3 and 4 of Table 2. The legs treated with the preparation of this invention exhibits significantly greater reduction from dry/damaged baseline state than the ammonium lactate control sites.

Figure 7:
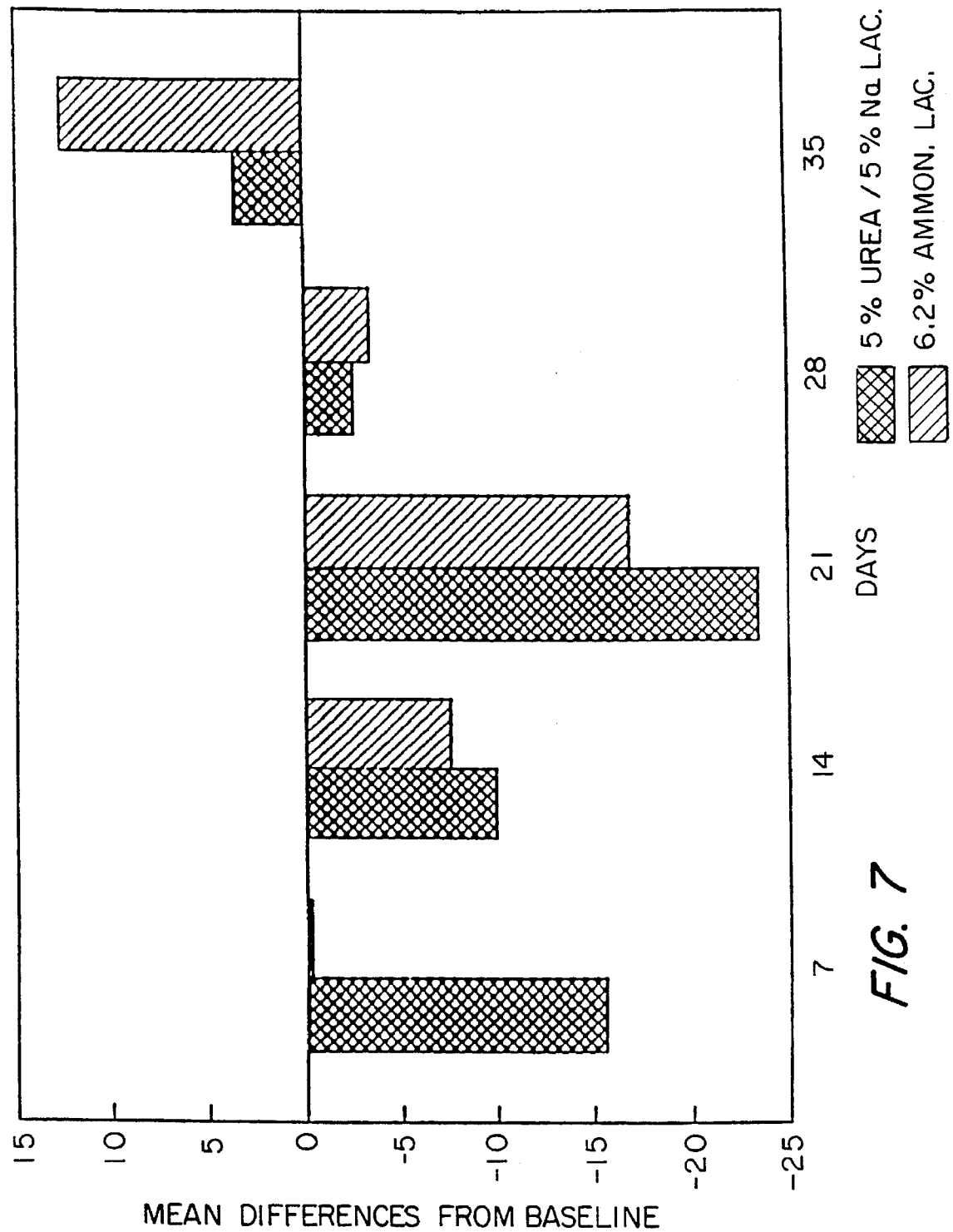
FIG. 7 compares flakiness measured using D'Squame™ disks on the severely dry skin treated as described in the legend of FIG. 5 above. The data were calculated as mean differences from the baseline. The cross-hatched bars depict data for treatment using the composition of this invention, and the hatched bars depict data for the ammonium lactate control.

Flakiness was assessed by analysis of D'Squame™ disks as described in Example 1. Assessments were made on days 0, 7, 14, 21, 28 and 35. Parallel to the rapid improvement of dry skin as determined by visual evaluation, analysis of D'Squame™ disks demonstrated rapid improvement of flakiness for these sites after the first week of treatment. FIG. 7 shows mean differences calculated as post-treatment minus baseline. Columns 5 and 6 of Table 2 give the actual test data. At the end of the study, at day 35, the urea/sodium lactate treated sites again exhibited a superior state.

Subjective burning and/or stinging was evaluated by the panelists, who rated the sensations according to the following scale:

0=no burning or stinging
1=mild burning or stinging
2=moderate burning or stinging
3=severe burning or stinging.

Figure 8:
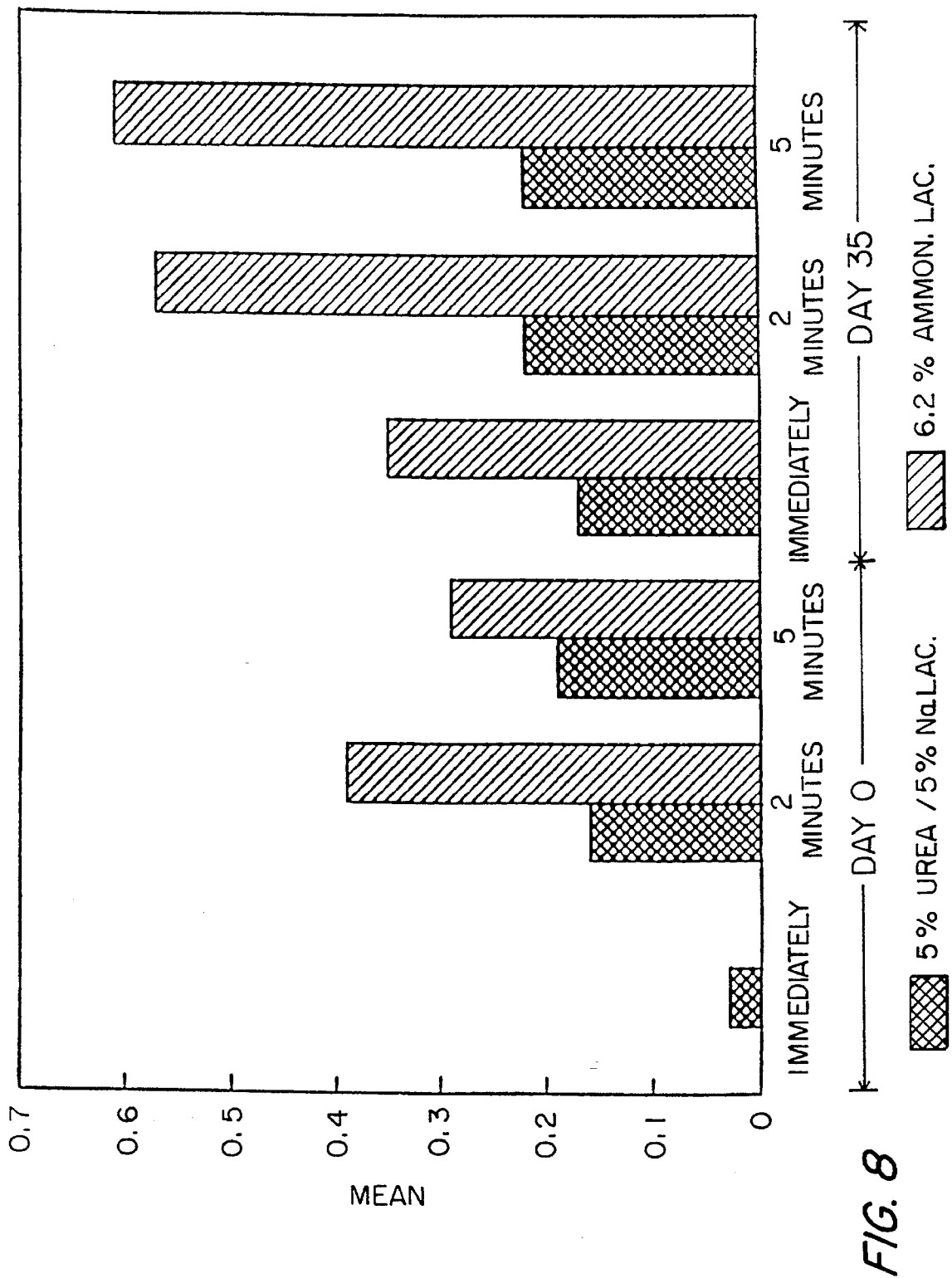
FIG. 8 gives mean subjective burning/stinging scores described by test subjects having severely dry skin treated as set out in the legend of FIG. 5 above. Both treatments were evaluated for burning/stinging potential at the beginning (day 0) and the end (day 35) of the study, immediately after application of the test materials and 2 and 5 minutes into treatment. The cross-hatched bars depict assessments of the treatment using the composition of the invention, and the hatched bars depict assessments of the ammonium lactate control.

The results are plotted in FIG. 8, data are given in Table 3. The composition of the invention caused less burning or stinging than the control.

TABLE 3

| | Subjective Burning/Stinging Comparison | |
|---|---|---|
| Time of Evaluation | Column 1 5.0% NaLac 5.0% Urea | Column 2 6.2% Ammon Lactate |
| Day 0 | | |
| Immediate | 0.03 | 0.00 |
| 2 Minutes | 0.16 | 0.39 |
| 5 Minutes | 0.19 | 0.29 |
| Day 35 | | |
| Immediate | 0.17 | 0.35 |
| 2 Minutes | 0.22 | 0.57 |
| 5 Minutes | 0.22 | 0.61 |

This study compared and contrasted a dry skin treatment using a urea/lactate composition of this invention with a commercially available dry skin product control containing ammonium lactate. The composition of this invention contained 10.0% by weight urea and 2.5% by weight sodium lactate in a water-in-oil emulsion. The control contained 14.0% by weight ammonium lactate in an oil-in-water emulsion.

The study was conducted in Winnipeg, Manitoba for a 35-day period from March through April 1992, during which the average temperature was −1° C. and the average relative humidity was 71.7%. Thirty female panelists were enrolled in the study, of whom 28 completed it. The study area was the lower leg. Both legs of each subject initially had a score of grade 3, graded according to the following scale:

0=smooth, no evidence of dryness
1=slightly dry skin
2=moderately dry skin, flaking, peeling
3=severely dry skin, flaking, peeling.

Figure 9:
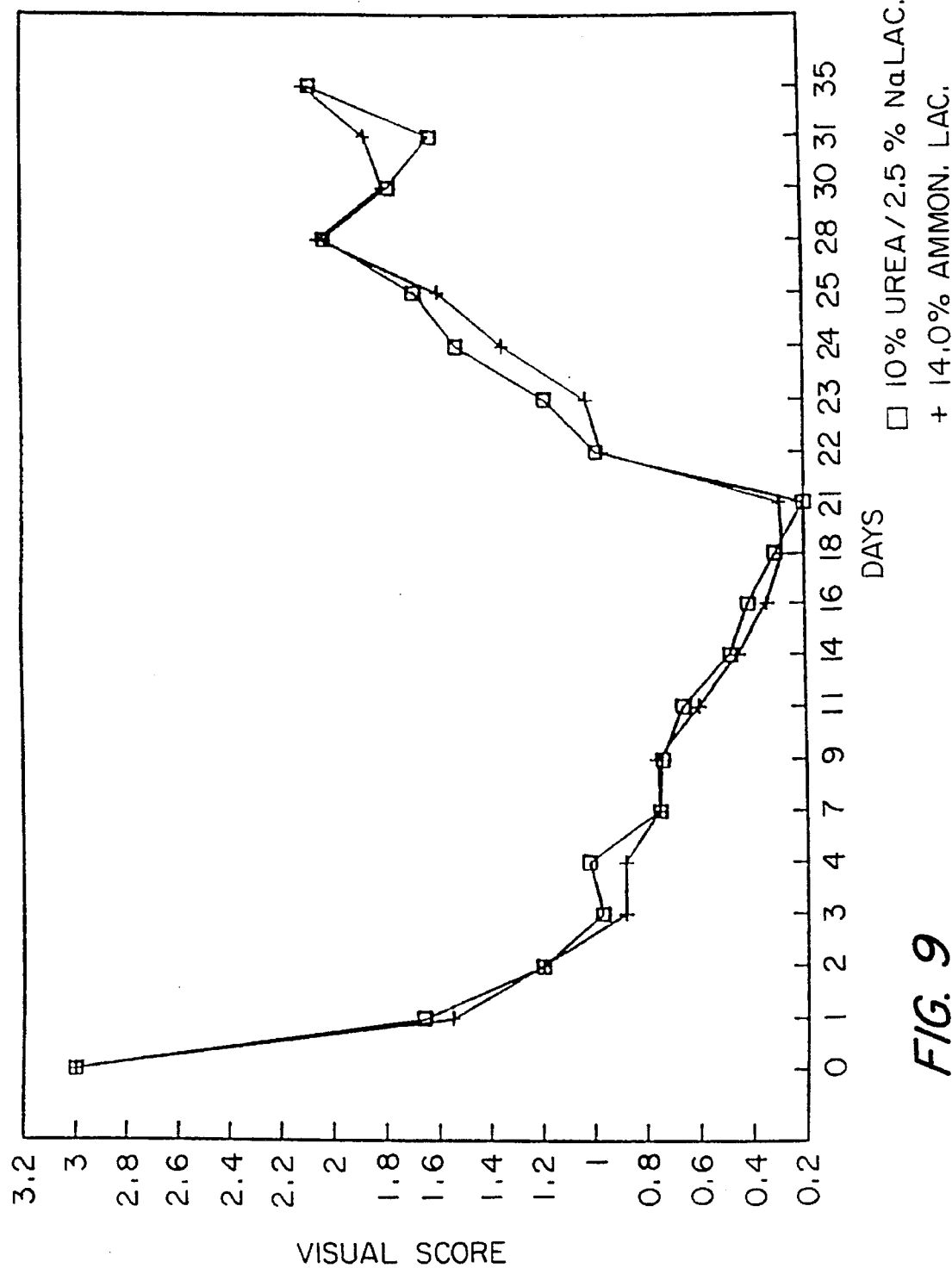
FIG. 9 gives mean visual dry skin scores in a randomized, double-blinded clinical test comparing a 2.5% sodium lactate/10% urea-containing water-in-oil emulsion of this invention with a commercial product containing 14.0% ammonium lactate in an oil-in-water emulsion. Test materials were applied to severely dry skin in 28 subjects twice daily for 21 consecutive days, and evaluations continued for 14 days after discontinuing treatment. On the "Visual Scores" axis, 3.0 denotes severely dry, fissured skin and 0.0 denotes perfectly healthy, moist skin.

Products were applied twice daily, the test material to one leg and the control to the other. The assignments were made in a randomized fashion; the study was double-blinded in design. Products were applied for 21 consecutive days, followed by a 14-day regression period. Evaluations were made on days 0, 1–4, 7, 9, 11, 14, 16, 18, 21–25, 28, 30, 32 and 35. Visual evaluations found the urea/sodium lactate-containing preparation of this invention to be an equally effective moisturizer as the control during the treatment phase. Flaking and peeling of the skin disappeared in most subjects over the first week. FIG. 9 shows the mean visual dry skin scores for both preparations. Actual test data are given in columns 1 and 2 of Table 4 below.

Figure 10:
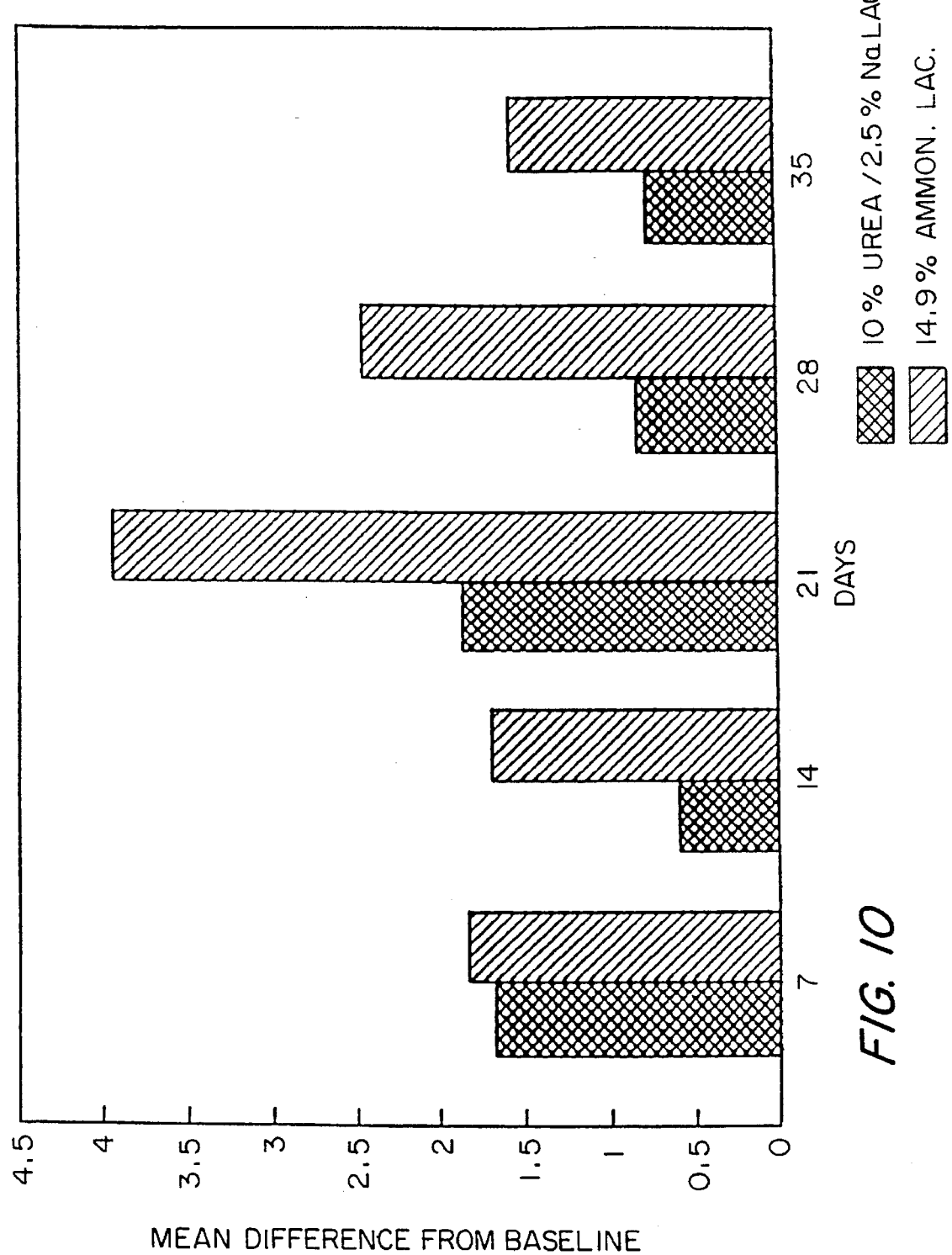
FIG. 10 compares trans-epidermal water loss measured on the severely dry skin treated as described in the legend of FIG. 9 above. The data were calculated as mean differences from the baseline. The cross-hatched bars depict data for treatment using the composition of this inventions, and the hatched bars depict data for the ammonium lactate control.

In addition to visual evaluation, trans-epidermal water loss (TEWL) was recorded with a ServoMed Evaporimeter™ (Stockholm, Sweden) as described above under Example 2. TEWL evaluations were made on days 0, 7, 14, 21, 28 and 35. As set out in FIG. 10, which shows mean differences calculated as post-treatment minus baseline, the TEWL data indicated less disturbance of the skin's barrier function for treatment with the product of this invention than for the ammonium lactate control. Data are given in columns 3 and 4 of Table 4.

TABLE 4

| | A Comparison of Another Ammonium Lactate With a Composition of the Invention | | | | | |
|---|---|---|---|---|---|---|
| Days | Column 1 Visual Dry Skin Scores 2.5% NaLac 10.0% Urea | Column 2 Visual Dry Skin Scores 14.0% Ammon Lactate | Column 3 TEWL 2.5% NaLac 10.0% Urea | Column 4 TEWL 14.0% Ammon Lactate | Column 5 D'Squames 2.5% NaLac 10.0% Urea | Column 6 D'Squames 14.0% Ammon Lactate |
| 0 | 3.00 | 3.00 | | | | |
| 1 | 1.66 | 1.55 | | | | |
| 2 | 1.20 | 1.20 | | | | |
| 3 | 0.97 | 0.88 | | | | |
| 4 | 1.02 | 0.88 | | | | |
| 7 | 0.75 | 0.75 | 1.68 | 1.84 | −31.09 | −33.05 |
| 9 | 0.74 | 0.76 | | | | |
| 11 | 0.66 | 0.60 | | | | |
| 14 | 0.48 | 0.45 | 0.60 | 1.69 | −24.46 | −28.72 |
| 16 | 0.41 | 0.34 | | | | |
| 18 | 0.31 | 0.28 | | | | |
| 21 | 0.20 | 0.29 | 1.86 | 3.94 | −28.56 | −29.79 |
| 22 | 0.98 | 0.96 | | | | |
| 23 | 1.18 | 1.02 | | | | |
| 24 | 1.52 | 1.34 | | | | |
| 25 | 1.68 | 1.59 | | | | |
| 28 | 2.02 | 2.04 | 0.84 | 2.46 | −18.92 | −16.84 |
| 30 | 1.77 | 1.79 | | | | |

TABLE 4-continued

A Comparison of Another Ammonium Lactate With a Composition of the Invention

| Days | Column 1 Visual Dry Skin Scores 2.5% NaLac 10.0% Urea | Column 2 Visual Dry Skin Scores 14.0% Ammon Lactate | Column 3 TEWL 2.5% NaLac 10.0% Urea | Column 4 TEWL 14.0% Ammon Lactate | Column 5 D'Squames 2.5% NaLac 10.0% Urea | Column 6 D'Squames 14.0% Ammon Lactate |
|---|---|---|---|---|---|---|
| 32 | 1.61 | 1.86 | | | | |
| 35 | 2.07 | 2.09 | 0.77 | 1.56 | −12.86 | −8.32 |

Figure 11:
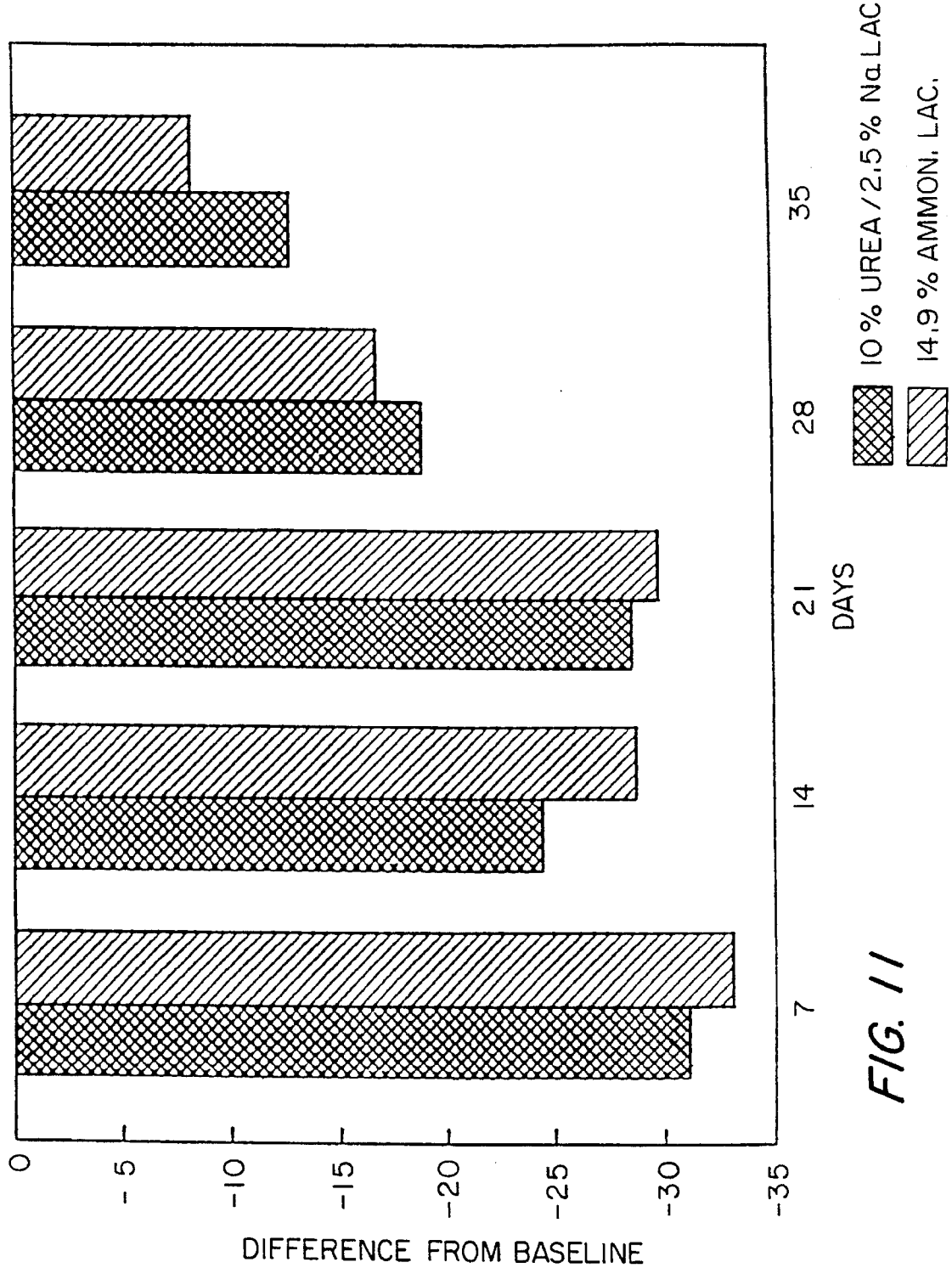
FIG. 11 compares flakiness measured using D'Squame™ disks on the severely dry skin treated as described in the legend of FIG. 9 above. The data were calculated as mean differences from the baseline. The cross-hatched bars depict data for treatment using the composition of this invention, and the hatched bars depict data for the ammonium lactate control.

Flakiness was assessed by analysis of D'Squame™ disks as described in Example 1. Assessments were made on days 0, 7, 14, 21, 28 and 35. Parallel to the rapid improvement of dry skin as determined by visual evaluation, analysis of D'Squame™ disks demonstrated rapid improvement of flakiness for these sites after the first week of treatment. FIG. 11 shows mean differences calculated as post-treatment minus baseline. Columns 5 and 6 of Table 4 give the actual test data. Test product and ammonium lactate control showed about equal effects.

Subjective burning and/or stinging was evaluated by the panelists, who rated the sensations according to the following scale:

0=no burning or stinging

1=mild burning or stinging

2=moderate burning or stinging

3=severe burning or stinging.

Figure 12:
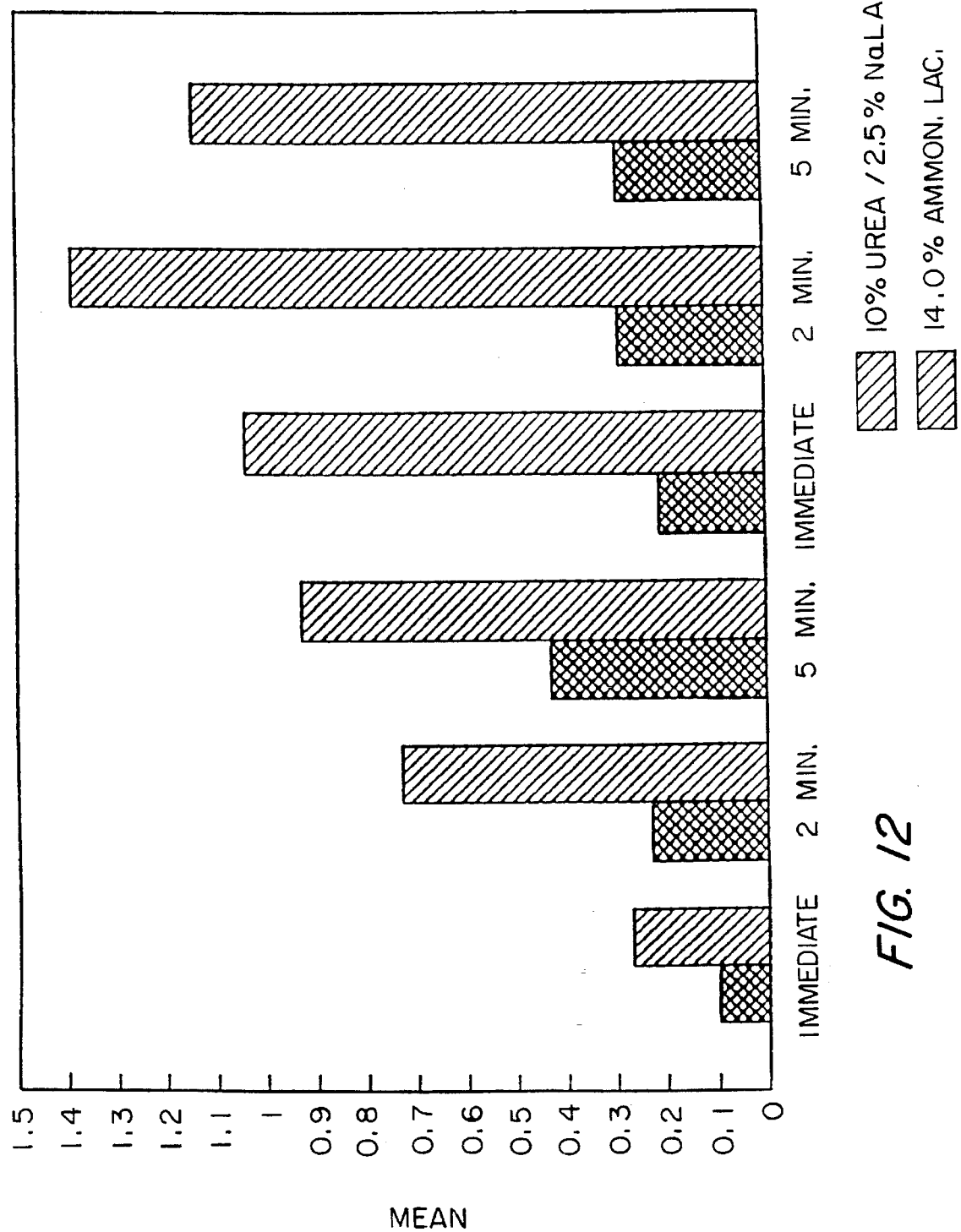
FIG. 12 gives mean subjective burning/stinging scores described by test subjects having severely dry skin treated as set out in the legend of FIG. 9 above. Both treatments were evaluated for burning/stinging potential at the beginning (day 0) and the end (day 35) of the study, immediately after application of the test materials and 2 and 5 minutes into treatment. The cross-hatched bars depict assessments of the treatment using the composition of the invention, and the hatched bars depict assessments of the ammonium lactate control.

The results are plotted in FIG. 12, data are given in Table 5. The composition of the invention caused significantly less burning or stinging than the control.

TABLE 5

Subjective Burning/Stinging Comparison

| Time of Evaluation | Column 1 2.5% NaLac 10.0% Urea | Column 2 14.0% Ammon Lactate |
|---|---|---|
| Day 0 | | |
| Immediate | 0.10 | 0.27 |
| 2 Minutes | 0.23 | 0.73 |
| 5 Minutes | 0.43 | 0.93 |
| Day 35 | | |
| Immediate | 0.21 | 1.04 |
| 2 Minutes | 0.29 | 1.39 |
| 5 Minutes | 0.29 | 1.14 |

The above description is for the purpose of teaching the person of ordinary skill in the art how to practice the present invention, and is not intended to detail all those obvious modifications and variations of it which will become apparent to the skilled worker upon reading the description. It is intended, however, that all such obvious modifications and variations be included within the scope of the present invention, which is defined by the claims that follow. The claims are meant to cover the claimed components and steps in any sequence which is effective to meet the objectives there intended, unless the context specifically indicates the contrary.

We claim:

1. In a urea composition for the treatment of dry skin, an improvement wherein the composition comprises from about 1% to about 15% by weight urea and from about 1% to about 10% by weight of an alkali or an earth metal salt of lactic acid in a cosmetically acceptable water-in-oil emulsion formulated so that, on application to affected skin areas, transepidermal water loss of the skin is controlled and disturbance of the epidermal barrier is minimized.

2. An improvement according to claim 1 wherein, on application to affected skin areas, the composition is substantially confined to the stratum corneum.

3. An improvement according to claim 1 wherein the alkali or earth metal salt of lactic acid is selected from the group consisting of sodium lactate, potassium lactate, calcium lactate, and mixtures thereof.

4. An improvement according to claim 3 wherein the alkali salt of lactic acid is sodium lactate.

5. An improvement according to claim 3 wherein the composition comprises from about 2% to about 5% by weight alkali salt of lactic acid and from about 2% to about 5% by weight urea.

6. An improvement according to claim 3 wherein the composition comprises from about 2% to about 4% by weight lactate and from about 5% to about 10% by weight urea.

7. A method for the treatment or prevention of dry skin comprising topically applying to affected skin areas a cosmetically acceptable water-in-oil emulsion containing from about 1% to about 15% by weight urea and from about 1% to about 5% by weight of an alkali or earth metal salt of lactic acid.

8. A method according to claim 7 wherein the alkali or earth metal salt of lactic acid is selected from the group consisting of sodium lactate, potassium lactate, calcium lactate, and a mixture of these salts.

9. A method according to claim 8 wherein the alkali salt is sodium lactate.

10. A method according to claim 8 wherein the emulsion comprises from about 1% to about 7% by weight of lactic acid and from about 1% to about 7% by weight urea.

11. A method according to claim 10 wherein the emulsion comprises about 5% by weight urea and about 5% by weight sodium lactate.

12. A method according to claim 8 wherein the emulsion comprises from about 1% to about 5% by weight lactate and from about 3% to about 15% by weight urea.

13. A method according to claim 12 wherein the emulsion comprises about 2.5% by weight sodium lactate and about 10% by weight urea.

14. A composition for the treatment or prevention of dry skin which comprises from about 1% to about 15% by weight urea and from about 1% to about 10% by weight of an alkali salt of lactic acid in a cosmetically acceptable water-in-oil emulsion.

15. A composition according to claim 14 wherein the alkali or earth metal salt of lactic acid is selected from the group consisting of sodium lactate, potassium lactate, calcium lactate, and a mixture of these salts.

16. A composition according to claim 15 wherein the alkali salt is sodium lactate.

17. A composition according to claim 15 wherein the composition comprises from about 1% to about 10% alkali or earth metal salt of lactic acid and from about 1% to about 10% urea.

18. A composition according to claim 17 wherein the composition comprises from about 2% to about 5% by weight lactate and from about 2% to about 5% by weight urea.

19. A composition according to claim 18 wherein the composition comprises about 5% by weight sodium lactate and about 5% by weight urea.

20. A composition according to claim 15 wherein the composition comprises from about 1% to about 5% by weight lactate and from about 3% to about 15% by weight urea.

21. A composition according to claim 20 wherein the composition comprises from about 2% to about 4% by weight lactate and from about 5% to about 10% by weight urea.

22. A composition according to claim 21 wherein the composition comprises about 2.5% by weight sodium lactate and about 10% by weight urea.

* * * * *